United States Patent [19]

Vermeulen et al.

[11] Patent Number: 5,602,033
[45] Date of Patent: Feb. 11, 1997

[54] COCCIDIOSIS VACCINE

[75] Inventors: Arno Vermeulen, Cuyk; Rein Dijkema, Oss; Jacobus J. Kok, Nijmegen, all of Netherlands

[73] Assignee: Akzo Nobel N.V., Arnhem, Netherlands

[21] Appl. No.: 371,947

[22] Filed: Jun. 27, 1989

[30] Foreign Application Priority Data

Jun. 27, 1988 [NL] Netherlands .................. 8801627

[51] Int. Cl.$^6$ .................................................. C12N 1/20
[52] U.S. Cl. ....................... 435/252.33; 435/320.1; 435/69.3; 435/172.3; 435/235.1; 435/252.3; 536/23.7; 536/23.1; 536/23.5; 530/350
[58] Field of Search .................. 435/69.1, 91, 172.3, 435/235, 252.3, 320.1; 536/27; 530/350; 935/18, 29, 31, 41, 56, 58, 63, 73

[56] References Cited

U.S. PATENT DOCUMENTS

| | | | |
|---|---|---|---|
| 4,639,372 | 1/1987 | Murray et al. | 424/88 |
| 4,724,145 | 2/1988 | Murray et al. | 424/88 |
| 4,874,705 | 10/1989 | Andrews et al. | 435/252.33 |
| 4,973,551 | 11/1990 | Condra | 435/69.7 |
| 5,028,694 | 7/1991 | Mewman et al. | 530/350 |
| 5,187,080 | 2/1993 | Andrews | 435/69.3 |
| 5,273,901 | 12/1993 | Jacobson et al. | 435/243 |
| 5,403,581 | 4/1995 | Binger | 424/191.1 |
| 5,496,550 | 3/1996 | Wallach et al. | 424/184.1 |

FOREIGN PATENT DOCUMENTS

| | | |
|---|---|---|
| 0135073 | 3/1985 | European Pat. Off. . |
| 0167443 | 6/1985 | European Pat. Off. . |
| 256536 | 2/1988 | European Pat. Off. ..... A61K 39/102 |
| 0519547 | 12/1992 | European Pat. Off. . |
| 8600528 | 1/1986 | WIPO .................. A61K 39/02 |

OTHER PUBLICATIONS

Danforth, H. D. et al, Avian Diseases, vol. 30(1), Jul. 23, 1995 pp. 37–42.

Young, R. A. et al, Proc. Nat'l. Acad. Sci, vol. 80(5) Mar. 1983, pp. 1194–1198.

Wisher, M. H., "Sporozoite Antigens of Coccidia", J. Cell Biochem. Suppl. 7A, p. 25, Abs. #0059, (1983).

Stotish, R. et al., "Isolation and In vitro translation of mRNA from *Eimera tenella*," Fed. Procd., #44, Abs. 5401, (1985).

Clarke et al Mol Biochem Parasitol vol. 22 pp. 79–87 (1987).

Jenkins et al Exp. Parasitol vol. 66 pp. 96–107 (1988).

M. C. Jenkins et al., "Identification and recombinant DNA cloning of immunodominant surface antigens of *Eimeria acervulina* sporozoites and merozoites", *Federation Proceedings*, vol. 46, No. 3, 1987, #2696.

H. Lillehoj et al., "Protection against *Eimeria acervulina* infection correlates with the T–cell response to the recombiant surface merozoite antigen", *The FASEB Journal*, vol. 2, No. 4, Mar. 15, 1988, #3403, p. A881.

M. Jenkins et al., "Cloning of cDNA encoding surface antigens of *Eimeria acervulina* sporozoites and merozoites: DNA sequence analysis and study of T–cell and B–cell epitopes", *The FASEB Journal*, vol. 2, No. 4, Mar. 15, 1988, #3399, p. A880.

Primary Examiner—James C. Housel
Assistant Examiner—Ginny Allen Portner
Attorney, Agent, or Firm—Mary E. Gormley; William M. Blackstone

[57] ABSTRACT

The present invention is concerned with a polypeptide of *Eimeria* which can be used for the immunization of poultry against coccidiosis. Furthermore, the invention comprises a DNA fragment of *Eimeria* coding for said polypeptide.

11 Claims, 5 Drawing Sheets

```
GLU  PHE  PRO  GLU  GLN  MET  PRO  PRO
G A A T T C C C T G A A C A A A T G C C T C C C
            10                    20

SER  ALA  ALA  ARG  ASP  ASP  LEU  GLU
T C C G C T G C T C G C G A T G A T C T C G A A
        30                40

ALA  GLY  LEU  LEU  GLU  PHE  GLU  ARG
G C T G G C C T C C T C G A G T T C G A G A G A
50              60                    70

ASP  GLU  ARG  ALA  ASP  PRO  SER  SER
G A T G A G C G C G C G G A C C C A T C G T C A
            80                    90

TRP  PRO  TYR  PRO  ARG  LEU  ALA  VAL
T G G C C T T A T C C A G A T T G G C T G T T
        100               110                 120

GLY  VAL  LEU  LYS  ASP  SER  ASN  GLY
G G T G T T C T C A A G G A T T C C A A C G G T
                  130                 140

SER  VAL  MET  VAL  PRO  ILE  ALA  PRO
T C A G T C A T G G T G C C C A T T G C C C C G
        150                   160

LYS  PHE  VAL  PRO  ARG  LEU  ARG  LYS
A A G T T T G T T C C A A G G C T C A G A A A G
170               180                   190

MET  ALA  PHE  ARG  VAL  ILE  VAL  GLU
A T G G C A T T C C G T G T C A T C G T C G A G
            200                   210

SER  GLY  ALA  GLY  ALA  ASN  ALA  GLY
T C C G G T G C T G G C G C G A A T G C T G G C
        220                   230              240

PHE  SER  ASP  GLU  GLU  TYR  ARG  ARG
T T C A G T G A C G A A G A G T A C A G A A G A
                  250                 260

ALA  GLY  ALA  GLU  ILE  ALA  SER  ASN
G C T G G A G C A G A G A T T G C G T C C A A C
            270                   280

ALA  ASP  ALA  VAL  ILE  ASN  GLY  ALA
G C C G A T G C A G T C A T C A A C G G A G C T
290                   300                   310

GLU  VAL  LEU  LEU  ARG  VAL  SER  ALA
G A G G T G C T G C T C C G C G T G T C A G C C
            320                   330
```

FIG. 2A

```
PRO  THR  PRO  GLU  MET  VAL  SER  ARG
C C A A C A C C G G A A A T G G T C T C C C G C
   340              350              360

MET  PRO  ARG  ASP  LYS  VAL  LEU  ILE
A T G C C C A G A G A C A A G G T G C T G A T C
               370              380

SER  TYR  LEU  PHE  PRO  SER  VAL  ASN
A G C T A C C T C T T C C C C A G C G T C A A C
             390              400

THR  GLN  ALA  LEU  ASP  MET  LEU  ALA
A C G C A A G C A T T A G A C A T G C T T G C A
410              420              430

ARG  GLN  GLY  VAL  THR  ALA  LEU  ALA
C G T C A A G G A G T C A C A G C C C T T G C T
               440              450

VAL  ASP  GLU  VAL  PRO  ARG  VAL  THR
G T G G A C G A A G T G C C A C G T G T C A C C
   460              470              480

ARG  ALA  GLN  LYS  LEU  ASP  VAL  LYS
A G A G C A C A A A A G C T A G A C G T T A A G
             490              500

SER  ALA  MET  GLN  GLY  LEU  GLN  GLY
T C T G C G A T G C A A G G C C T C C A G G G C
             510              520

TYR  ARG  ALA  VAL  ILE  GLU  ALA  PHE
T A T C G C G C A G T C A T T G A A G C A T T C
530              540              550

ASN  ALA  LEU  PRO  LYS  LEU  SER  LYS
A A C G C A C T C C C A A A G C T C A G C A A G
               560              570

ALA  SER  ILE  SER  ALA  ALA  GLY  ARG
G C G T C C A T C A G C G C T G C T G G C C G T
   580              590              600

VAL  GLU  ALA  ALA  LYS  VAL  PHE  VAL
G T T G A G G C T G C C A A G G T T T T C G T T
               610              620

ILE  GLY  ALA  GLY  VAL  ALA  GLY  LEU
A T C G G T G C C G G T G T T G C C G G T C T C
               630              640

GLN  ALA  ILE  SER  THR  ALA  HIS  GLY
C A G G C T A T T T C A A C T G C C C A T G G T
650              660              670
```

FIG. 2B

```
LEU GLY ALA GLN VAL PHE GLY HIS
T T G G G T G C A C A A G T T T T C G G T C A T
        680               690

ASP VAL ARG SER ALA THR ARG GLU
G A T G T G C G C T C C G C A A C A C G C G A G
    700             710             720

GLU VAL GLU SER CYS GLY GLY LYS
G A G G T C G A A T C T T G T G G T G G A A A G
            730             740

PHE ILE GLY LEU ARG MET GLY GLU
T T C A T T G G C T T G A G A A T G G G G A G
        750             760

GLU ALA GLU VAL LEU GLY GLY TYR
G A A G C T G A A G T T C T C G G A G G C T A T
770             780                 790

ALA ARG GLU MET GLY ASP ALA TYR
G C A C G C G A A A T G G G T G A T G C G T A C
            800             810

GLN ARG ALA GLN ARG GLU LEU ILE
C A G A G G G C C C A A A G A G A G T T G A T T
        820             830             840

ALA ASN THR ILE LYS HIS CYS ASP
G C A A A C A C A A T C A A G C A C T G T G A C
            850                 860

VAL VAL ILE CYS THR ALA ALA ILE
G T T G T C A T A T G T A C C G C T G C C A T C
            870             880

HIS GLY LYS PRO SER PRO LYS LEU
C A C G G A A A G C C T T C T C C G A A G C T T
890                 900                 910

ILE SER ARG ASP MET LEU ARG SER
A T C T C A C G C G A C A T G C T G C G C T C A
                920             930

MET LYS PRO GLY SER VAL ILE VAL
A T G A A G C C T G G C T C T G T C A T T G T G
        940             950             960

ASP ILE ALA THR GLU PHE GLY ASP
G A C A T T G C A A C T G A A T T C G G C G A T
            970             980

THR ARG SER GLY TRP GLY GLY ASN
A C G C G C T C T G G A T G G G G A G G A A A T
        990             1000
```

FIG. 2C

```
VAL  GLU  VAL  SER  PRO  LYS  ASP  ASP
G T T G A G G T T T C C C C A A G G A C G A C
1010            1020            1030

GLN  VAL  VAL  VAL  ASP  GLY  ILE  THR
C A G G T C G T G G T C G A C G G C A T C A C T
        1040            1050

VAL  ILE  GLY  ARG  LYS  ARG  ILE  GLU
G T C A T T G G A C G C A A A C G C A T T G A A
    1060            1070            1080

THR  ARG  MET  PRO  VAL  GLN  ALA  SER
A C C C G C A T G C C A G T C C A G G C T T C A
            1090            1100

GLU  LEU  PHE  SER  MET  ASN  ILE  CYS
G A G C T G T T C T C C A T G A A C A T C T G C
        1110            1120

ASN  LEU  LEU  GLU  ASP  LEU  GLY  GLY
A A C T T C T C G A A G A T C T A G G T G G C
1130            1140            1150

GLY  SER  ASN  PHE  ARG  VAL  ASN  MET
G G C A G C A A C T T C C G C G T C A A C A T G
        1160            1170

ASP  ASP  GLU  VAL  ILE  ARG  GLY  LEU
G A C G A C G A A G T T A T C A G A G G A T T G
    1180            1190            1200

VAL  ALA  VAL  TYR  GLN  GLY  ARG  ASN
G T T G C C G T C T A T C A A G G C C G C A A C
            1210            1220

VAL  TRP  GLN  PRO  PRO  GLN  PRO  THR
G T G T G G C A G C C C C C C A G C C A A C G
        1230            1240

PRO  VAL  SER  ARG  THR  GLU  PHE
C C C G T C T C A A G A A C G G A A T T C
1250            1260
```

FIG. 2D

COCCIDIOSIS VACCINE

The invention relates to a DNA fragment and an *Eimeria* polypeptide coded by this, recombinant DNA which contains the particular DNA fragment, host cells with this recombinant DNA and vaccines against coccidiosis which are based on these products.

Coccidiosis is a disease which is caused by intracellular parasites, protozoa, of the subphylum Apicomplexa and the genus *Eimeria*. These parasites multiply in cells which form part of the gastrointestinal tract and digestive organs of their hosts.

Due to the increasing intensive production, the damage which is caused by these parasites in the poultry industry has risen alarmingly in recent decades. The losses which poultry farmers in the Netherlands suffer every year run into millions of guilders; the loss in 1986 was about 13 million guilders. In the same year a loss of U.S. $300 million was suffered in the U.S., despite the use of coccidiostats.

The pathogens of coccidiosis in chickens can be subdivided into nine different types, i.e. *Eimeria acervulina, E. maxima, E. tenella, E. necatrix, E. brunetti, E. mitis, E. praecox, E. mivati* and *E. hagani*. However, some people doubt the existence of the last two types. All of these types have only the chicken as host and display a high degree of tissue specificity. The life cycles of the said types are, however, similar.

The types do differ in their pathogenic effect on chickens, the type of chicken also playing a role; thus, a spring chicken will be subjected to a great deal of damage by a parasite such as *E. acervulina* or *E. maxima* because these parasitise large portions of the small intestine, where food digestion plays a major role.

During the life cycle, the *Eimeria* parasites pass through a number of stages. The infectious stage (the sporulating oocyst) is taken in orally and passes into the stomach of the chicken, where the shell of the cyst bursts open as a result of the grinding action. The four sporocysts, which this oocyst contains, are released and pass into the duodenum, whereby they are exposed to bile and digestive enzymes. As a result, an opening is made in the sporocyst wall and the sporozoites present in the sporocyst are released. These sporozoites are mobile and search for suitable host cells, for example epithelium cells, in order to penetrate and to reproduce. Depending on the type, this first reproduction phase lasts 20 to 48 hours and several tens to hundreds of merozoites are formed, which each again penetrate a new host cell and reproduce. After two to sometimes five of these asexual reproduction cycles, the intracellular merozoites grow into sexual forms, the male and female gametocytes. After fertilization of the female by a male gamete, a zygote is formed which creates a cyst wall around itself. This oocyst leaves the host cell and is driven out with the faeces. If the temperature and humidity outside the chicken are relatively high and, at the same time, there is sufficient oxygen in the air, the oocyst can sporulate to the infectious stage.

Thus, no intermediate host is needed for transfer of the parasite from chicken to chicken. It is therefore conceivable that with a high degree of occupation of the available surface area the infection pressure in a chicken farm rapidly increases.

The parasite can be combatted in various ways.

In addition to using good management, coccidiosis can be combatted by using combatting agents which frequently are mixed in the feed or drinking water. However, these agents have suffered a drop in effectiveness in recent years, partly because of the high genetic capacity of the parasite to develop a resistance towards various combatting agents. In addition, a number of these agents leave residues in the meat which can give rise to problems on consumption.

Immunological prophylaxis would, therefore, constitute a much better combatting method. It is known that chickens which have lived through a sufficiently high infection are able to resist a subsequent contact with the same type of *Eimeria*. Resistance towards *Eimeria* can also be induced by infecting the birds several times with low doses of oocysts or with oocysts of weakened (non-pathogenic) strains. However, controlled administration to, specifically, large numbers of chickens for slaughter is a virtually insurmountable problem in this case. Inactivated vaccines therefore appear to be the only remaining solution.

An inactivated vaccine can consist of an antigen originating from the parasite, possibly with an adjuvant.

As an alternative for an antigen isolated from parasites, it is possible to use a product prepared with the aid of recombinant DNA technology, a technique which can be carried out according to known methods.

Moreover, vaccination can be carried out by administering a live host organism such as a bacterium, a fungus or a virus in which a gene coding the antigen has been incorporated. This organism then ensures adequate long-term synthesis of antigen so that the immune system of the chicken is adequately stimulated.

At the same time it is possible synthetically to reproduce the antigen or parts thereof and to administer this to the birds in an immunologically recognizable and stimulating form, for example bonded to a carrier protein in the presence of an adjuvant.

According to the present invention it is possible to use a polypeptide or an immunogenic equivalent or part thereof, which is coded by a deoxypolynucleotide which is derived from *E. acervulina* and is present as an insertion in the plasmid pEa1A, with which the *Escherichia coli* strain K12JA221 has been transformed, which has been deposited with the Centraal Bureau voor Schimmelcultures, Baarn (The Netherlands) under deposit number CBS 143.88, for the immunization of poultry against coccidiosis.

Furthermore, the present invention comprises also the use of a polypeptide of an *Eimeria* specie or an immunogenic equivalent or part thereof, which is coded by a deoxypolynucleotide derived of an *Eimeria* specie and which hybridizes with the inserted deoxypolynucleotide sequence, for the immunization of poultry against coccidiosis.

The abovementioned plasmid pEa1A is prepared by the method given in the experimental section, which is explained here schematically with the aid of FIG. 1.

The phage λgt11 (ref. 4) was treated with the restriction enzyme EcoRI, for which it possesses a single restriction site. A cDNA, prepared on the basis of *E. acervulina* mRNA, is inserted in this restriction site: λgt11Ea1A. After treatment with the restriction enzymes KpnI and SacI, a phage fragment is isolated from the recombinant phage thus obtained, which fragment consists of the said cDNA and flanking DNA sections originating from the locality of the EcoRI restriction site, in the LacZ gene, of λgt11. The plasmid pUC18 (ref. 6) was likewise treated with KpnI and SacI and then ligated with the previously mentioned phage fragment containing cDNA:pUC18/Ea1A.

The nucleotide sequence which is determined for the cDNA section of this insertion is given in FIG. 2. Likewise the amino acid sequence derived herefrom.

It is known that for a given amino acid frequently several different codons (triplets of nucleotide bases) can code in the DNA. Thus, the codon for GLU (glutamic acid) is for example GAT or GAA, etc. It is obvious that for the expression of the polypeptide with the amino acid sequence according to FIG. 2 (or a fragment thereof) use can likewise be made of a DNA with a similar alternative codon composition.

For expression of the polypeptide according to the invention, use can also be made of a DNA fragment which is obtained by isolating a DNA fragment from the genomic DNA or the cDNA of *Eimeria* species which, according to known techniques under stringent conditions, hybridizes with the cDNA section of the plasmid Ea1A. If desired, a DNA fragment of this type can also possess, in addition to the cDNA section just mentioned, additional flanking DNA pieces which are coding for polypeptides.

DNA fragments of this type obtained by hybridization and also recombinant DNA molecules which contain these fragments likewise form part of the present invention.

Polypeptides which are coded by these DNA fragments and have protective, immunizing properties also form part of the invention.

In addition, fragments of these polypeptides, which can be used for immunization of poultry against coccidiosis, also form part of the invention. Various methods are known for detecting such usable polypeptide fragments (termed epitopes) within a known or unknown amino acid sequence. On the basis of a known amino acid sequence, these epitopes can, for example, be determined experimentally with the aid of the screening techniques described in patent publications WO 84/03564 and WO 86/06487.

In addition, a number of regions of the polypeptide, with the stated amino acid sequence, can be designated epitopes on the basis of theoretical considerations and structural agreement with epitopes which are now known. The determination of these regions was based on a combination of the hydrophilicity criteria according to J. P. Hopp and K. R. Woods (ref. 5) and the secondary structure aspects according to P. Y. Chou and G. D. Fasman (ref. 8).

The following regions contain probable epitopes for antibodies:

$Leu_{20}$—$Arg_{37}$
$Gly_{41}$—$Met_{51}$
$His_{232}$—$Cys_{245}$
$Glu_{325}$—$Gly_{334}$
$Gly_{335}$—$Val_{346}$
$Gly_{355}$—$Glu_{366}$

T-cell epitopes which may be necessary can likewise be derived on theoretical grounds with the aid of Berzofsky's amphiphilicity criterion (ref. 9).

For immunization against coccidiosis infection in accordance with the present invention it is also possible to use, for example, anti-idiotype antibodies or antigen-binding fragments thereof. Such antibodies are directed against the idiotype of antibodies, which, in turn, are directed against the polypeptide according to the invention. The immunogenic equivalents of the polypeptide according to the invention which have been indicated above are understood to mean, inter alia, anti-idiotype antibodies of this type.

The intended immunization can, for example, be effected by administering the present polypeptide, or an immunogenic section or equivalent thereof, as such to the birds, or by administering to the birds to be immunized a microorganism which has been genetically modified by a recombinant DNA and which is able to produce the polypeptide, or an immunogenic section or equivalent thereof, in situ.

For immunization of poultry against coccidiosis in accordance with the present invention, it is possible, on the one hand, to administer the present polypeptides, fragments or immunogenic equivalents as such to the birds or, on the other hand, if desired to administer microorganisms which by genetic manipulation have acquired the ability to produce the present polypeptides etc. "Subunit vaccines" is a frequently used term for the first case and the term "vector vaccines" is usually used for the second case—we will also adopt this nomenclature here.

The subunit vaccines according to the invention in general contain the polypeptides in purified form, optionally in the presence of a pharmaceutically acceptable excipient. The polypeptide can optionally be covalently bonded to a non-related protein, which, for example, can be of advantage in the purification of the fusion product. Examples are β-galactosidase, protein A, prochymosine, blood clotting factor Xa, etc.

The polypeptides for such applications can be prepared with the aid of known methods, such as by isolation from *E.acervulina* or other *Eimeria* species, by means of recombinant DNA techniques or by peptide synthesis.

If desired, the polypeptides can also be modified in vivo or in vitro by, for example, glycosylation, amidation, carboxylation or phosphorylation.

In vector vaccines, the polypeptide product according to the invention is made up by a genetically manipulated organism which is itself administered to the individual to be immunized and which maintains itself for some time, or even reproduces, in the body. Diverse organisms can be used as the host for this purpose, such as, for example, bacteria such as *Escherichia coli, Bacillus,* or *Salmonella,* or viruses such as cowpox or avian pox virus. With host organisms of this type, the polypeptide can express itself as a surface antigen. In this context fusion of the said polypeptide with OMP proteins or pilus proteins of *Escherichia coli* or synthetic provision of signal and anchor sequences which are recognized by the organism are conceivable. It is also possible that the said immunogenic polypeptide, if desired as part of a larger whole, is released inside the animal to be immunized. In all of these cases it is also possible that one or more immunogenic products will find expression which generate protection against various pathogens and/or against various antigens of a given pathogen.

BRIEF DESCRIPTION OF THE FIGURES

FIG. 2: shows the nucleotide sequence of the M13 clones.

EXAMPLE 1

Sporulation of *E. acervulina* oocysts

Figure 1:
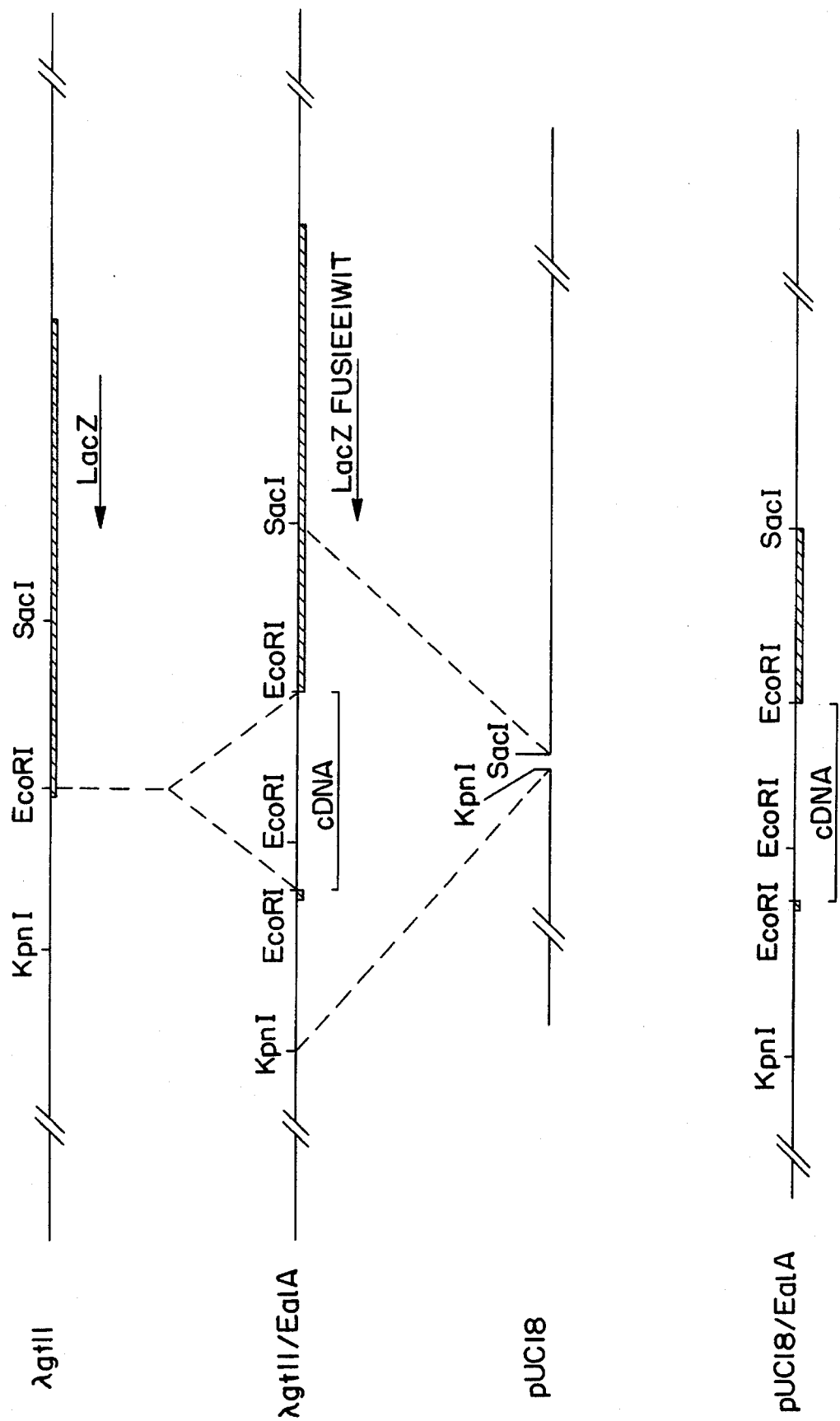
FIG. 1: shows further characterization of an immunopositive clone designated *E. acervulina* 1A.

A suspension of $5\times10^8$ *E. acervulina* oocysts in 60 ml $10^{-4}$M sodium dithionite was centrifuged, after which the pellet was washed once with 100 ml sterile water. The cells were resuspended in 500 ml 2% potassium bichromate and then incubated under the influence of strong aeration for 7 hours at 30° C. The oocysts were then collected by centrifuging and washed three times with 200 ml sterile water.

Isolation of RNA

For the isolation of RNA (ref. 1) the cell pellet was taken up into 2.8 ml of buffer containing 10 mM Tris acetate (pH 7.6), 75 mM sodium acetate, 1% SDS, 2 mM EDTA, 0.2 mg/ml proteinase K and 10 mM vanadyl ribonucleoside complexes. The oocysts were destroyed by vortexing for 60 seconds (max) in the presence of 13 g glass beads (Φ0.5 mm). 5 ml of phenol was added to the total extract and the mixture was vortexed for a further 60 seconds. After centrifuging, the supernatant liquor was pipetted off and again extracted with an equal volume of phenol/chloroform/isoamyl alcohol (25:24:1). RNA was precipitated after adding 2.5 volume ethanol and the resulting precipitate was dissolved in 800 μl Tris 10 mM, EDTA 0.1 mM pH 7.6 ($T_{10}E_{0.1}$), after which the product was extracted a further twice with an equal volume of phenol/chloroform/isoamyl alcohol (25:24:1) and twice with chloroform/isoamyl alcohol (24:1) and then precipitated with ethanol. PolyA$^+$-RNA was isolated by means of oligo(dT)-cellulose chromatography (ref. 2). Approximately 100 μg polyA$^+$-RNA was isolated from $5 \times 10^8$ oocysts.

cDNA synthesis

PolyA$^+$-RNA was converted to cDNA by means of the enzyme MMLV reverse transcriptase. For this purpose 25 μg polyA$^+$-RNA was dissolved in 90 μl of water and denatured for 5 minutes at 20° C. by adding mercury methyl hydroxide to 10 mM, after which β-mercaptoethanol was added to 45 mM and the mixture incubated for a further 3 minutes at 20° C. The enzyme reaction was carried out in 190 μl buffer containing 4 μg oligo(dT)$_{15}$, 150 U RNAsin®, 20 mM Tris (pH 7.6), 30 mM KCl, 4 mM dithiothreitol (DTT), 2 mM MgCl$_2$, 1 mM of each dNTP and 3000 U MMLV reverse transcriptase. The reaction was stopped after 1 hour's incubation at 37° C. by adding 10 μl 0.5M EDTA. After extraction with an equal volume of phenol/chloroform/isoamyl alcohol (25:24:1), the RNA/DNA hybrid was precipitated by adding ammonium acetate to 2M and 2.5 volumes ethanol. The combined action of the enzymes DNA-polymerase I and RNase H (ref. 3) results in the synthesis of the second string. The pellet was dissolved in 960 μl of buffer containing 20 mM Tris (pH 7.6), 5 mM MgCl$_2$, 100 mM (NH$_4$)$_2$SO$_4$, 0.6 mM β-NAD, 16 U RNase H, 200 U DNA-polymerase I and 20 U DNA-ligase (*E.coli*). The incubation time was 1 hour at 12° C. and then 1 hour at 22° C., after which the reaction was stopped by adding an equal volume of phenol/chloroform/isoamyl alcohol (25:24:1) and precipitating with ethanol.

Before the cDNA was cloned in a vector suitable for this purpose it was first modified. cDNA (5 μg) was dissolved in 100 μl of buffer containing 30 mM sodium acetate (pH 5.6), 50 mM NaCl, 1 mM ZnSO$_4$ and 21 U Mung Bean Nuclease. After incubation for 30 minutes at 37° C. the reaction was stopped by adding EDTA to 10 mM and Tris to 25 mM. After extraction with phenol/chloroform/isoamyl alcohol (25:24:1) the mixture was desalinated over a Sephadex G50 column.

The following were added to the eluate (125 μl): Tris pH 7.6 to 50 mM, EDTA to 2.5 mM, DTT to 5 mM, S'-adenosylmethionine to 0.5 μm and 100 U EcoRI-methylase. After incubation for 30 minutes at 37° C., the reaction was stopped by heating for 15 minutes at 65° C., after which 1/10 volume of a solution containing Tris-HCl 100 mM, MgCl$_2$ 100 mM and NaCl 500 mM (pH 7.5) was added, and, at the same time, each dNTP to 1 mM and 12.5 U Klenow DNA-polymerase. The reaction was stopped by adding an equal volume of phenol/chloroform/isoamyl alcohol (25:24:1) after incubating for 60 minutes at 22° C. The supernatant liquor was precipitated after adding 350 μl H$_2$O and 50 μl 3M sodium acetate (pH 5.6) with 500 μl isopropanol. After dissolving in 100 μl H$_2$O, the pellet was desalinated over Sephadex G50 and the eluate precipitated with ethanol.

After dissolving the pellet in 24 μl H$_2$O, ligation was carried out in 50 μl by adding 2 μg EcoRI linker, Tris-HCl (pH 8.0) to 30 mM, MgCl$_2$ to 10 mM, dithiothreitol to 10 mM, ATP to 1 mM, gelatin to 0.1 mg/ml and 10 U T$_4$DNA-ligase. The reaction was stopped after 16 hours' incubation at 4° C. by heating (for 15 minutes at 70° C.) after which cutting was carried out with restriction endonuclease EcoRI in 210 μl buffer containing 100 mM Tris-HCl (pH 7.6), 50 mM NaCl, 10 mM MgCl$_2$, 2.5 mM DTT and 500 U EcoRI. After 90 minutes' incubation at 37° C., the reaction was stopped by means of extraction with an equal volume of phenol/chloroform/isoamyl alcohol (25:24:1). The supernatant liquor was precipitated with 2.5 volume ethanol after adding sodium acetate (pH 5.6) to 300 mM cDNA and linkers were separated by means of a Biogel A15m column. The cDNA was precipitated with ethanol, after which the precipitate was dissolved in Tris-HCl 10 mM, EDTA 0.1 mM (pH 7.6). The cDNA molecules were then cloned in phage λgt11 (4).

Screening of the cDNA banks with antibodies directed against sporozoites showed a positive reaction in 1 per 1000 phage clones. These antibodies were previously purified over protein A Sepharose®, and then diluted four times with 1×Tris salt (Tris-HCl 10 mM, NaCl 150 mM, pH 8.0)+0.05% Tween 20+10% Foetal Calf Serum (FCS) and incubated for two hours at 37° C. with the filter.

The filter was then washed 4 times, for 10 minutes each time, with 50 ml 1×Tris salt+0.05% Tween 20. For the second antibody incubation a conjugate of goat-antimouse antibodies and alkaline phosphatase was used (diluted 1 per 7500 in 1×Tris salt+0.05% Tween 20+10% FCS) and incubated for 30 minutes at 37° C., after which the filter was washed as described after the 1st antibody incubation. The colour reaction was carried out in Tris-HCl 100 mM, NaCl 100 mM, MgCl$_2$ 10 mM, (pH 9.6), in which 0.33 mg/ml Nitroblue tetrazolium and 0.17 mg/ml 5-bromo-4-chloro-3-indolyl phosphate were dissolved. The filters were evaluated after 30 minutes incubation at room temperature.

An immunopositive clone was plaque-purified and this clone, designated *E. acervulina*1A clone (λgt11Ea1A) was further characterized (FIG. 1).

Phage DNA was isolated (ref. 2) and cut with the enzyme EcoRI.

The EcoRI fragments were subcloned in M13mp18 and pBR327. In addition, the complete cDNA fragment was subcloned in pUC18. Restriction maps were made of these subclones in pBR327 and the nucleotide sequence of the M13 clones was determined completely (FIG. 2).

For expression of the fusion protein, a lysogenic strain was made in *E. coli* Y1089$^-$ (ref. 4). The protein was purified over a Proto-Sorb LacZ column (Promega®) before it was used in a chicken protection experiment.

EXAMPLE 2

Protection against *E. acervulina* infection

The fusion protein produced by clone λgt11Ea1A in *Escherichia coli* Y1089$^-$ was purified in accordance with Example 1. For this purpose the product was brought together with avridine (ref. 7) in a suitable buffer, such that 1 ml suspension contained 1 mg avridine and 0.1 mg product. This material was injected intramuscularly into 4-week-old chickens (white Leghorns) in a dose of about 50 μg product per chicken. After two weeks this innoculation was repeated with an identical dose. Ten days later the chickens were infected with 50,000 sporulated *E. acervulina* oocysts which were administered orally (challenge). The numbers of oocysts in the faeces were counted daily. As controls, chickens were also injected with killed sporozoites and merozoites of E. acervulina and with β-galactosidase, all suspended in 500 μg avridine per dose. The results of this experiment are given in Table 1. Each group contained five chickens and the numbers of oocysts are listed per chicken and are the total of four days excretion (day 3 to day 6 post-infection inclusive).

TABLE 1

| Antigen | "Immunisation" dose per chicken per injection | Oocyst excretion per chicken after challenge | % inhibition with respect to control |
|---|---|---|---|
| Sporozoites | $1 \times 10^7$ | $82.8 \times 10^7$ | 47 |
| Merozoites | $1 \times 10^7$ | $20.9 \times 10^7$ | 87 |
| LacZ-Ea1A | 50 μg | $62.2 \times 10^7$ | 60 |
| β-galactosidase | 50 μg | $143.7 \times 10^7$ | 8 |
| Challenge control | — | $155.8 \times 10^7$ | — |

Challenge: contained 50,000 sporulated oocyst of E. acervulina in 1 ml 15% sucrose solution and was administered orally.

EXAMPLE 3

Antibodies

Antibodies evoked in chickens with the product obtained according to Example 1 were found to react, in dilutions of up to 1:1600, against components of the invasive stages, sporozoites and merozoites of types such as E. tenella, E. acervulina and E. maxima. These components are mainly localized in the foremost section of these stages where the penetration organelles, rhoptries and micronema are also located. In some chickens the antibodies were found to react around the Refractile Body of the sporozoites, especially of E. tenella.

EXAMPLE 4

Protection against E. tenella infection

The purified fusion protein was brought together with dioctadecylammonium bromide (DDA) in a suitable buffer, such that 1 ml of suspension contained 0.5 mg DDA and about 50 μg fusion protein. This material was injected intramuscularly into 3–4 week old chickens (white Leghorns) in a dose of about 50 μg fusion protein per chicken. After two weeks the chickens were orally challenged with 7500 sporulated E. tenella oocysts (Weybridge Strain). Seven days after the challenge injection the chickens were killed and lesions were scored on both ceca of each chicken. The lesions were scored according to the guide-lines of Johnson and Reid (ref. 10). The results of this experiment are given in Table 2. From this, it is clear that a protein or a fragment thereof comprising at least a portion corresponding to the Ea1A polypeptide can be obtained from other Eimeria species. Each group contained five chickens.

TABLE 2

| Antigen | Immunisation dose | Lesion score ± SD |
|---|---|---|
| LacZ-Ea1A | 50 μg | 2.5 ± 1.2 |
| β-galactosidase | 50 μg | 3.5 ± 0.0 |
| challenge control | — | 3.3 ± 0.5 |

SD = standard deviation

EXAMPLE 5

Isolation and identification of Ea1A related DNA sequences from E. tenella

Construction of a cDNA library from E. tenella

For the construction of a cDNA library from E. tenella sporulated oocysts exactly the same procedure was followed as described in Example 1, except that the final cDNA preparation was cloned in phage λgt10 instead of phage λgt11 (4).

Screening of the E. tenella cDNA library with E. acervulina DNA

The 296 bp EcoRI fragment from pUC18/Ea1A was labeled with digoxigenin-dUTP by random priming, exactly following the protocol going with the "DNA labeling and detection kit, non-radioactive" from Boehringer, Mannheim (Cat. No. 1093657).

Filters containing immobilized DNA from the E. tenella cDNA library described above were prepared as described by Maniatis et al. (2) and probed by the freshly denatured (10 min. 95° C.), labeled E. acervulina fragment for 16 hours at 42° C. according to the manufacturer's instructions. Filters were washed as follows: twice for fifteen minutes with 2×SSC, 0.1% (w/v) SDS (1×SSC is 0.015 mol/l sodium citrate pH 7.0 plus 0.15 mol/l NaCl) at room temperature, twice for fifteen minutes with 1×SSC, 0.1% (w/v) SDS at 68° C., twice for thirty and once for fifteen minutes with 0.1×SSC, 0.1% (w/v) SDS at 68° C. and twice with PBS-tween (7.65 g/l NaCl, 0.91 g/l $Na_2HPO_4.2H_2O$, 0.21 g/l $KH_2PO_4$, 0.05% (v/v) Tween 80, pH 7.3) for 15 minutes at room temperature.

The filters were then reacted with a 1:5000 dilution in PBS-tween of polyclonal sheep anti-digoxigenin Fab-fragments, conjugated to alkaline phosphatase, for thirty minutes at room temperature. After washing the filters for four times fifteen minutes with PBS-tween at room temperature and once for fifteen minutes with 0.01M Tris-HCl pH 8.0, 0.15M NaCl, binding of the alkaline phosphatase to the filters was detected upon incubation with a solution of 0.33 g/l Nitroblue tetrazolium and 0.17 g/l 5-bromo-4-chloro-3-indolyl-phosphate in 0.1M Tris-HCl pH 9.6, 0.1M NaCl, 0.01M $MgCl_2$. One out of every 400 λgt10 E. tenella clones reacted with the E. acervulina probe; ten of these, called E. tenella1A1 to 10 (λgt10Et1A1 to 10) were plaque-purified. λgt10Et1A1 together with the Escherichia coli strain BNN102 have been deposited with the Centraal Bureau voor Schimmelcultures, Baarn (The Netherlands).

REFERENCES

1) J. Pasternak et al.: Mol. & Bioch. Par. 3 (1981), 133–142.
2) T. Maniatis et al.: Molecular Cloning (Cold Spring Harbor Laboratory) 1982.
3) U. Gubbler et al.: Gene 25 (1983), 263–269.
4) T. V. Huynk et al.: DNA Cloning Techniques: A Practical Approach; D. Glover Oxford (1984).
5) J. P. Hopp et al.: Proc.Natl.Acad. Sci. U.S.A. 78 (1981), 3824–3828.
6) Ganish-Perron C.: Gene 33 (1985) 103–119.
7) K. E. Jensen in "Advances in carriers and adjuvants for Veterinary Biologics" ed. R. M. Nervig, P. M. Gough, M. L. Kaeberle, C. A. Whetstone. Iowa State Univ. Press. 1986, pp. 77–91.
8) P. Y. Chou et al.: Advances in Enzymology 47 (1987), 145–148.
9) M. F. Good et al.: Science 235 (1987), 1059–1062.

10) J. Johnson and W. M. Reid; Exp. Parasitology 28 (1970), 30–36.

We claim:

1. An isolated and purified DNA molecule derived from *Eimeria acervulina,* wherein said DNA molecule encodes an antigenic polypeptide consisting of the amino acid sequence of FIG. 2.

2. An isolated and purified DNA molecule derived from *E. acervulina* which consists of the deoxynucleotide sequence shown in FIG. 2.

3. An isolated and purified DNA molecule derived from *Eimeria acervulina,* which encodes an antigen consisting of an antigenic fragment of the polypeptide having the amino acid sequence shown in FIG. 2.

4. A plasmid vector comprising the DNA molecule of claim 1.

5. A phage vector comprising the DNA molecule of claim 1.

6. The plasmid vector of claim 4, wherein the plasmid is pEa1A.

7. The plasmid vector of claim 4, wherein the plasmid is pUc18/Ea1A.

8. A host cell transformed with a vector comprising the DNA molecule of claim 1.

9. A host cell according to claim 8, wherein the host cell is a bacterium.

10. The host cell of claim 9, wherein the host cell is *Escherichia coli.*

11. The phage vector of claim 5, wherein the phage is selected from the group consisting of lambda gt11Ea1A and lambda gt10Ea1A.

* * * * *